United States Patent [19]
Weissman et al.

[11] Patent Number: 5,661,188
[45] Date of Patent: Aug. 26, 1997

[54] THERAPEUTIC USES FOR SODIUM 2-MERCAPTOETHANESULPHONATE (MESNA)

[75] Inventors: Irith Weissman, K. Bialik; Batya Kristal, Kibbutz Evron; Shifra Sela, Kfar Veradim; Shaul Shahsa, Nahariya, all of Israel

[73] Assignee: Medical Research Foundation and Infrastructure Development for Health Services—Nahariya Hospital Branch, Nahariya, Israel

[21] Appl. No.: 483,867

[22] Filed: Jun. 7, 1995

[51] Int. Cl.⁶ .................................................. A61K 31/10
[52] U.S. Cl. ............................................................ 514/711
[58] Field of Search ................................... 514/711, 719

[56] References Cited

U.S. PATENT DOCUMENTS

| | | | |
|---|---|---|---|
| 4,623,742 | 11/1986 | Scheffler et al. | 558/81 |
| 4,929,607 | 5/1990 | Scheffler et al. | 514/110 |

OTHER PUBLICATIONS

MEXAN Uroprotector, ASTA Pharma AG, Weismullerstrasse, D–6,000 Frankfort 1 FRG (Dec. 1990).
Drug Evaluation Monographs, MESNA, Micromedex, Inc. vol. 83, Mar. 31, 1995.

"Free Radicals: From Basic Science to Medicine," VI Biennial Meeting, International Society for Free Radical Research, Torino (Italy), Volume of Abstracts, Jun. 16–20, 1992.

Cardio Science, 3(3): 179–887, Sep. 1992. Abstract.

Pharmacol–Res, 25 Suppl 1:85–6, Feb.–Mar. 1992. Abstract.

Ann–Oncol, 3 Suppl 2:S115–8, Apr. 1992. Abstract.

Primary Examiner—Phyllis G. Spivack
Attorney, Agent, or Firm—Lowe, Price, LeBlanc & Becker

[57] ABSTRACT

Uses for the compound sodium mercaptoethanesulphonate, commonly known as mesna are disclosed. The appropriate periodic administration of said compound to a patient or the addition of the compound to a preservation solution for a donor organ can prevent reperfusion injury. Likewise, the prescribed periodic administration of mesna to a patient whose peritoneum is about to be violated will aid in avoiding peritonitis.

31 Claims, 3 Drawing Sheets

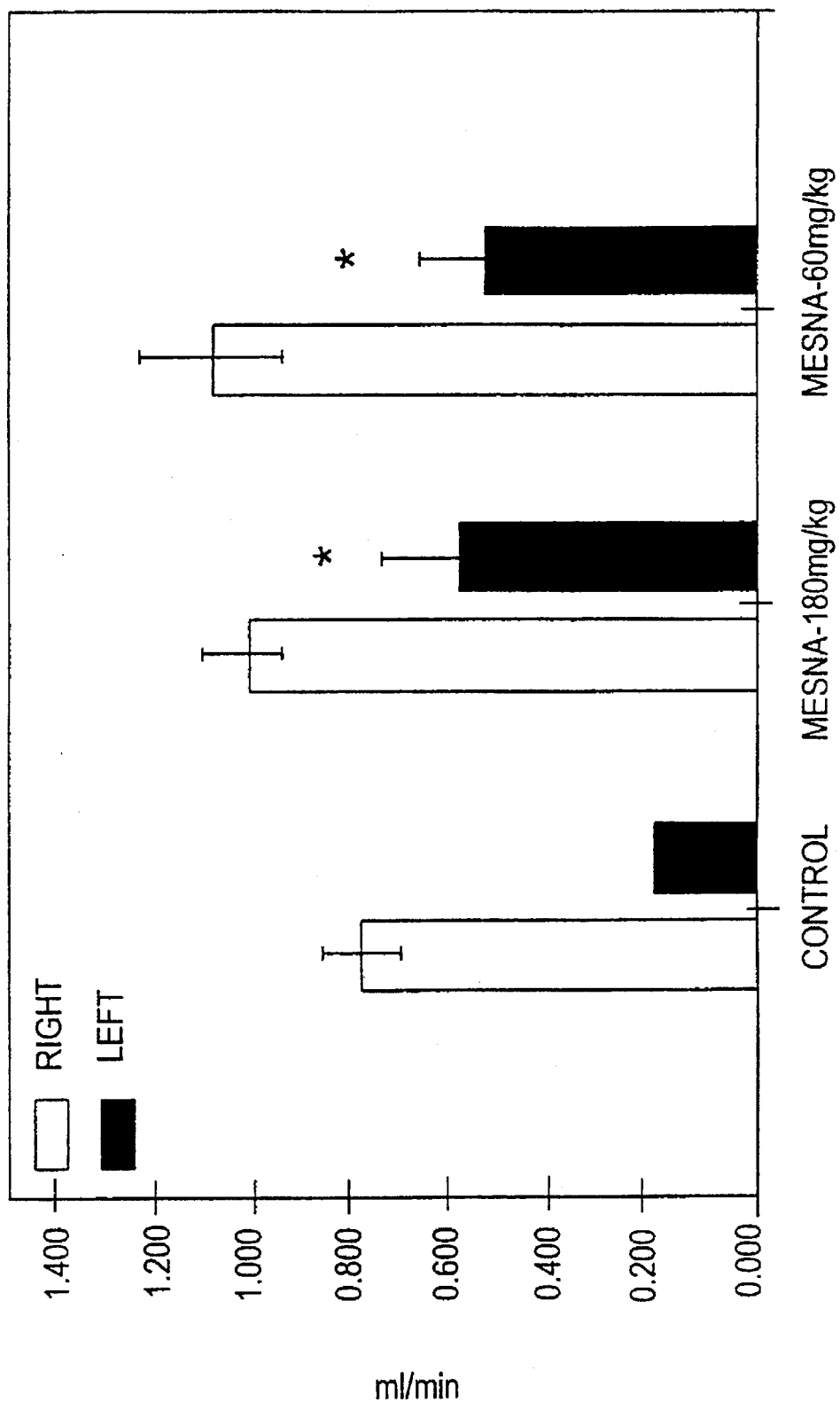

THERAPEUTIC USES FOR SODIUM 2-MERCAPTOETHANESULPHONATE (MESNA)

TECHNICAL FIELD

The present invention relates to the use of sodium 2-mercaptoethanesulphonate, particularly in association with organ transplants and in conjunction with avoiding peritonitis and for the prevention of acute ischemic renal failure.

BACKGROUND ART

Mesna, also know as Uromitexan®, is the common name for the compound sodium-mercaptoethanesulphonate. The compound mesna is hygroscopic, freely soluble in water, sparingly soluble in methanol and practically insoluble in conventional organic solvents. The compound mesna has been used for the prevention of urinary tract toxicity caused by various anti-tumor drugs, such as Endoxan® (ifosfamide), Holoxan® (trofosfamide) and Ixoten®. When mesna is employed for the foregoing purpose, side effects such as irritations of the veins or hypersensitivity reactions are extremely rare if mesna is used in a single dose of 60 mg mesna/kg body weight. However, if mesna is administered in excess of this dosage, nausea, retching and diarrhea have been observed. Mesna has also been employed in low doses, such as 21.5 mg per kg, as a reliable protection against the urotoxic effects of chemotherapeutic drugs, e.g., oxazaphosphorine derivatives, particularly, cyclophosphamide.

In toxicity tests, the LD 50 values determined for rats and mice after i.v. or i.p. administration are between 1,200 and 2,000 mg/kg; after oral administration in mice, greater than 6,000 mg/kg; and in rats about 4,500 mg/kg. In dogs, death was observed after intravenous doses of 400 mg/kg and above, but not after oral doses of up to 2,000 mg/kg. Accordingly, mesna is indicated to exhibit beneficial effects when used to protect a patient against the ravages of chemotherapy.

There is much literature available relating to the use of mesna. In U.S. Pat. No. 4,623,742, at column 9, the sodium salt of 2-mercaptoethanesulphonic acid or the disodium salt of the corresponding disulfide metabolite is recommended as an active neuroprotective agent. However, read in context, the foregoing refers only to protection against the toxic effects of chemicals used to control cancer diseases. This is explicitly described at lines 34-48 of the same column. Moreover, at column 10, lines 10-12, the curative effect of the compounds is defined as the recidive- and metastasis-free survival of the tumor-carrying animals over 90 days. In a related patent by the same inventors, U.S. Pat. No. 4,929,607, mesna is disclosed at column 5, line 13, but appears to involve a reaction product thereof with another compound to treat cancer diseases and to produce immunosuppression in humans and animals.

A comprehensive treatise on mesna is entitled MEXAN Uroprotector, ASTA Pharma AG, Weismullerstrasse, D-6, 000 Frankfort 1 FRG (December 1990). This paper describes the protective effects of mesna against chemotherapeutic drugs. At page 11, paragraph 4, the nephroprotective property of mesna is described as follows:

As witnessed by the results of animal experiments conducted by Klein and coworkers (91), Uromitexan [mesna] has also a nephroprotective effect: Mice given 600 mg/kg Holoxan® in combination with 300 mg/kg mesna did not show any kidney lesions, while mice treated with such large Holoxan® doses alone evidenced renal injuries.

At page 12 of the MEXAN publication, the author explains that both mesna and dimesna pass unchanged through the hepatic vasculature, and are neither taken up into the liver cells nor excreted in bile. In the kidneys, dimesna is said to be subject to glomerular filtration and is subsequently reabsorbed, whereupon reduction to the pharmacologically active thiol form takes place in the renal tubular epithelium.

At page 28 of the MEXAN publication, it is questioned whether mesna affects the immunosuppressive efficacy of the oxazaphosphorines. Several workers, the article relates, noticed that five out of eight patients receiving Endoxan® and mesna were found to reject the transplant. Thus, it could not be established that this finding was related to the administration of mesna. Irrespective of the foregoing, since mesna was used in conjunction with Endoxan®, it would reasonably have been expected that the compound was merely exhibiting its known activity of protecting against chemotherapeutic agents.

Another description of mesna's uses appears in a monograph from Micromedex, Inc., at volume 83. In addition to reiterating mesna's use in conjunction with chemotherapeutic drugs, the article also mentions mucolytic therapy, in treating chronic bronchitis. Nevertheless, the authors conclude that mesna's efficacy was no greater than that of hypertonic saline.

In the abstracts from the VI Biennial Meeting of Free Radicals: From Basic Science to Medicine, International Society for Free Radical Research, Torino (Italy), Jun. 16-20, 1992, analogs of mesna are described wherein, instead of the sodium salt, the arginine salt of mercaptoethanesulphonic acid is employed. The arginine salt was synthesized to overcome the possible osmotic imbalance caused by a sodium overload resulting from high dose administration of mesna. At page 5.26, in the penultimate sentence, it is stated that the salification with arginine was chosen for its lack of toxicity and for its potentially positive effects of enhancing nonspecific immune response and host responses to tumors. Accordingly, it appears that argimesna (AR), like mesna, finds its principal role in counteracting the adverse effects of chemotherapeutic drugs.

However, unlike mesna, argimesna has been indicated to exhibit antioxidant properties in rabbit myocardium. At page 9.14 of said abstracts, argimesna is evaluated as a protective agent against ischemia and reperfusion damage in isolated and perfused Langendorff rabbit hearts. In the results reported, the authors state that in aerobic perfusion, AR did not produce any significant alteration of systolic and diastolic pressure. Before and during ischemia and reperfusion, AR delayed and reduced the rate of diastolic pressure on reperfusion and increased the recovery of systolic pressure. In the last sentence, the authors state that their data indicate "AR [at] $10^{-6}$M has a protective effect against ischaemia and reperfusion damage: in our opinion, AR could work as reduced equivalent donor able to reduce the oxygen toxicity."

The same information described above is reported by the same authors in *Cardio Science*, 3:179-87 (1992). In other articles describing the activity of argimesna, namely, *Pharmacol-Res*, 25 Suppl 1:85-6 (1992) and *Ann-Oncol*, 3 Suppl 2:S115-8 (1992), the compound is described as being a new uroprotective agent that is safe and active in the prevention of hemorrhagic cystitis from IFO.

Previous attempts have been made to employ certain drugs containing thiol groups as antioxidants.

DISCLOSURE OF THE INVENTION

An object of the present invention is a method for avoiding reperfusion injury in a donor organ following transplantation of the organ.

Another object of the present invention is a method for avoiding reperfusion injury in a donor organ subjected to ischemia prior to transplantation.

A further object of the present invention is a method for avoiding ischemic reperfusion injury to an organ due to a medical procedure.

Yet another object of the present invention is a method for avoiding peritonitis.

Additional objects, advantages and other features of the invention will be set forth in part in the description which follows and in part will become apparent to those having ordinary skill in the art upon examination of the following or may be learned from the practice of the invention. The objects and advantages of the invention may be realized and obtained as particularly pointed out in the appended claims.

According to the present invention, the foregoing and other objects are achieved in part by a method for avoiding reperfusion injury in a donor organ following transplantation of said organ, which method comprises periodically administering a therapeutically effective amount of the compound mesna to the patient-recipient of the transplanted organ.

A further aspect of the present invention is a method for avoiding reperfusion injury in a donor organ subject to ischemia during the period prior to transplantation, which method comprises maintaining the donor organ in a preservation solution after removal from the donor and prior to implantation in the recipient, wherein the preservation solution comprises a therapeutically effective amount of the compound mesna to prevent reperfusion injury.

Another aspect of the present invention is a method for avoiding reperfusion injury to an organ subject to ischemia due to a medical procedure, which method comprises periodically administering, prior to said medical procedure, a therapeutically effective amount of mesna to a patient about to undergo a medical procedure subjecting an organ to ischemia.

Yet another aspect of the present invention is a method for avoiding peritonitis in a patient, which method comprises periodically administering to said patient a therapeutically effective amount of the compound mesna prior to violation of the patient's peritoneum.

Another aspect of the invention is a method for avoiding peritonitis in a patient whose peritoneum has been violated, which method comprises periodically administering to said patient a therapeutically effective amount of the compound mesna.

Yet another aspect of the present invention is a method of transplanting an organ, which method comprises: removing the organ from a donor; maintaining the organ in a preservation solution; and implantating the organ in a recipient, wherein the preservation solution comprises a therapeutically effective amount of the compound mesna, to prevent reperfusion injury in the organ due to ischemia.

Another aspect of the present invention is a method for avoiding acute renal failure due to ischemia, which method comprises periodically administering, prior to said medical procedure, a therapeutically effective amount of mesna to a patient.

An additional aspect of the present invention is a method of transplanting an organ, which method comprises: removing the organ from a donor; maintaining the organ in a preservation solution; and implanting the organ in a recipient, wherein the preservation solution comprises a therapeutically effective amount of the compound mesna to prevent reperfusion damage in the organ due to ischemia.

Additional objects and advantages of the present invention will become readily apparent to those skilled in this art from the following detailed description, wherein only the preferred embodiment of the invention is shown and described, simply by way of illustration of the best mode contemplated for carrying out the invention. As will be realized, the invention is capable of other and different embodiments, and its several details are capable of modifications in various obvious respects, all without departing from the invention. Accordingly, the description is to be regarded as illustrative in nature, and not as restrictive.

BRIEF DESCRIPTION OF DRAWINGS

FIG. 2a depicts the glomerular filtration rate (GFR) data on rats.

FIG. 2b shows the fractional excretion of sodium (FENa) determined under the same conditions as in FIG. 2a.

DESCRIPTION OF THE INVENTION

Figure 1:
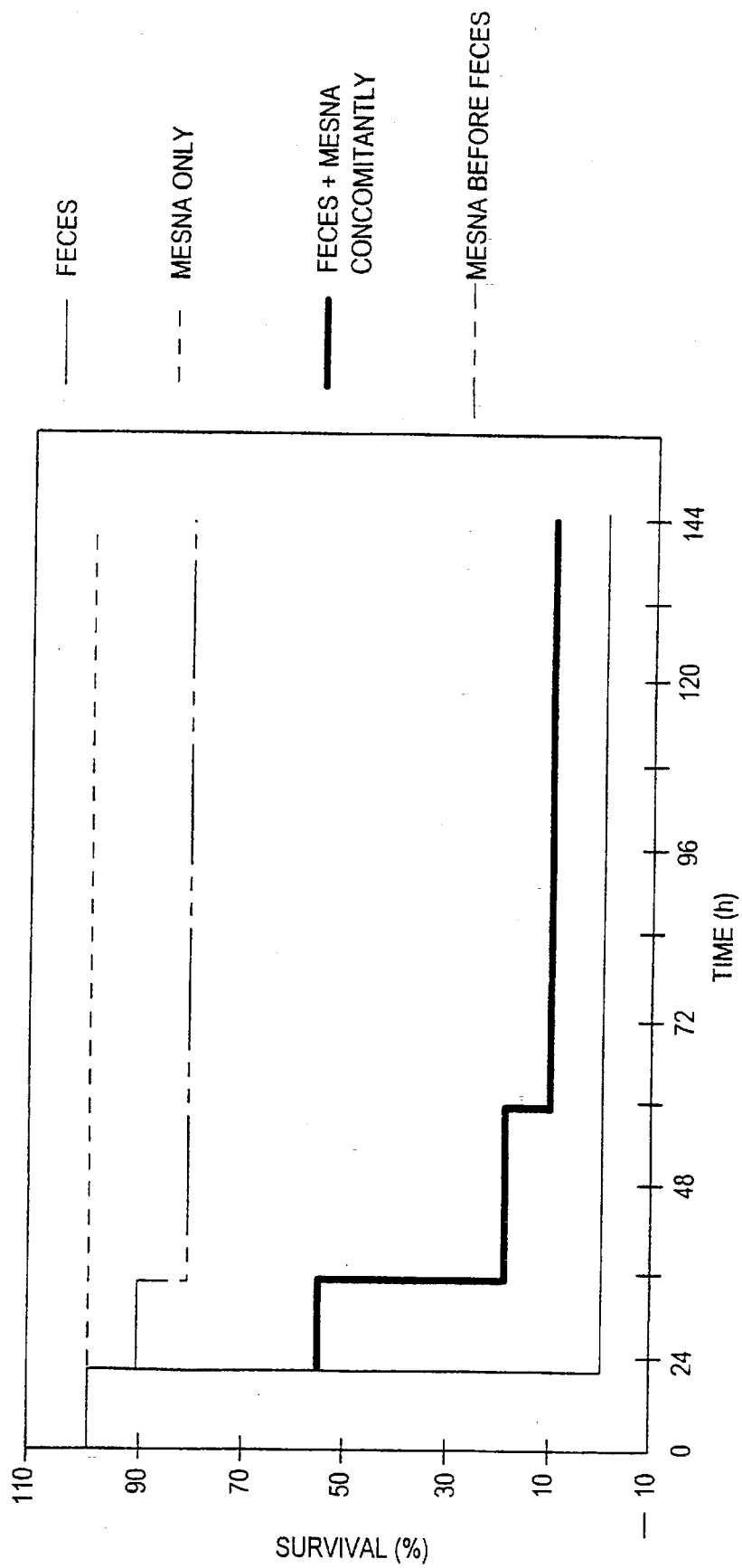
FIG. 1 graphically depicts the survival of rats after induction of peritonitis.

After extensive investigation and experimentation, new uses for the compound mesna have been discovered. Based upon the prior uses of mesna, these discoveries are considered quite unexpected.

An embodiment of the present invention comprises a method for avoiding reperfusion injury in a donor organ following transplantation of said organ, which method comprises administering a therapeutically effective amount of the compound mesna periodically to the patient-recipient of said transplanted organ. This embodiment has general applicability; it is particularly useful in the transplantation of a kidney.

The initial dosage of mesna employed for kidney recovery after ischemia is about 60 to about 80 mg/kg. As used throughout this disclosure, including the claims, the dosages characterized as "mg/kg" refer to milligrams per kilogram of body weight of the patient to which compound mesna is administered. Mesna can be administered in any conventional manner. However, mesna is preferably administered as a bolus or administered in an initial stage as a bolus followed by administration in an aqueous solution without a carrier. After administration of the initial dosage, it is preferred to administer mesna at a maintenance dosage of about 30 mg/kg/hour.

In accordance with the present invention, mesna is employed as the sodium salt, without any other active ingredients and without any variations, e.g., homologs or analogs. Mesna has been found to offer the best potential for kidney recovery after ischemia, especially on glomerular filtration rate (GFR). The operative mechanism involved in preventing acute renal failure due to ischemia employing mesna is not known. Presumably, antioxidation plays a role in the improvement of GFR; however, it is theorized that the negative charge of mesna has a beneficial effect.

Tubular necrosis of donor kidneys may result due to the ischemic period prior to transplantation, as during transportation of the kidney from the donor to the recipient. Whatever the mechanism, mesna will prevent acute tubular necrosis of donor kidneys, due to the ischemic period before transplantation. It is, therefore, another embodiment of the present invention to employ mesna to avoid reperfusion injury in a donor organ prior to actual implantation of the organ.

Donor organs are conventionally maintained in a preservation solution, typically containing antioxidants, after removal from a donor and prior to implantation. In accordance with an embodiment of the present invention, mesna is incorporated in a preservation solution in which a donor organ is maintained after removal from a donor and prior to implantation. The amount of mesna added to the preservation solution is a therapeutically effective amount to prevent reperfusion injury to the donor organ, preferably to prevent reperfusion injury to a kidney due to ischemia. A therapeutically effective amount of mesna can be easily determined by routine experimentation by one having ordinary skill in the art.

The changes in osmolarity and pH of the preservation solutions after addition of mesna to such solutions have been determined. It is believed that mesna, due to its thiol group, is an antioxidant. It is generally accepted that reperfusion injury is caused by reactive oxygen species (ROS). Acting as an antioxidant, mesna will abolish ROS damage. It is assumed that the same mechanism, i.e., generation of ROS, is involved in inducing acute renal failure by nephrotoxins, such as drugs, toxins and contrast media.

In another embodiment of the present invention, reperfusion injury to an organ subject to ischemia due to a medical procedure is avoided by administering, prior to the medical procedure, a therapeutically effective amount of mesna to the patient about to undergo the medical procedure which would subject the organ to ischemia, such as medical procedures which expose patients to a high risk of developing ischemic renal failure. Thus, this embodiment is applicable to the avoidance of ischemic reperfusion injury to a kidney as a result of surgery, and to the prevention of ischemic reperfusion injury to a heart as a result of open heart surgery.

Another embodiment of the present invention comprises the use of mesna to prevent or avoid peritonitis in a patient. After extensive experimentation and investigation, it was found that the administration of mesna to a patient is effective for preventing and avoiding peritonitis, such as prior to the violation of the patient's peritoneum. For example, where the body cavity of a patient is expected to be violated by exposing the peritoneum, as by surgical intervention, the administration of mesna can avoid peritonitis. In such a situation, it is preferable to administer mesna three time a day at a dosage of about 120 mg/kg. As stated earlier, it is believed that the negative charge of mesna has a beneficial effect, especially in preventing peritonitis, wherein the survival rate is improved due to the mesna action.

It was quite unexpected that mesna was found to be effective in avoiding peritonitis.

EXAMPLE

Fifty 10–12 week old male Sprague-Dawely rats weighing 250 gr approximately, were used in all experiments. Animals were fed a normal diet (AIN-76) and water ad libitum. The rats were divided into 5 groups, 10 in each group.

Group A: Control group, no treatment.
Group B: Control group, only mesna, injected i.p. 120 mg/kg three times daily.
Groups C, D and E: All were induced for peritonitis.
To induce peritonitis, feces was injected in two steps as follows: a preliminary injection at day 0 of 1.5–2 ml/kg was given. After 6 days, a total dose for induction of peritonitis in groups C, D and E was 16 ml of feces suspension per kg body weight, given in a single injection.
Group C: Feces only.
Group D: Mesna was given concomitantly with the single injection of feces on the sixth day and then injections continued 3 times a day until the rats died, in a dose of 40 mg mesna/kg per injection.
Group E: Mesna was injected from day 3 to day 6. On the sixth day, concomitant injections of feces and mesna were given, followed by injections of mesna, 3 times a day like group D.

Feces suspension for peritonitis induction was prepared as follows:

Fecal pellets from healthy rats were collected, weighed and ground. The ground feces was dispersed in tap water, one gram in 25 ml water, mixed well, sedimented and the clear suspension used for each injection.

RESULTS:

Mortality rates.

All the animals in Group B which received only mesna injection into the peritoneal cavity survived exactly like the control group.

All the rats injected with fecal suspension only, group C, died in the first twenty-four hours.

Rats belonging to group D receiving a lethal dose of feces simultaneously with mesna, 120 mg/day, 4 rats out of the 10 died in the first 24 hours; 4 other rats died after 40 hours; and 2 rats remained alive, but sick and weak for another day, then died too.

Rats belonging to group E, given mesna for three days before injection of the otherwise lethal dose of feces, 8 out of 10 animals survived. These animals were followed for 5 days after induction of peritonitis. They received mesna injections for 3 more days in the amount of 120 mg/day. These 8 rats stayed alive and consumed food as usual after the first $2\geq4$ hours, looked healthy, and their behavior seemed to be like the rats in the control group. Two animals from this group died on the first day after the lethal fecal dose injection.

Rectal temperature measurements.

It was found that one of the early signs that predicted a rat's situation and the severity of the rat's peritonitis was a drop in body temperature; the temperature of the rats in groups A and B remained normal, 37° C.

The temperature in the rats in group C (only feces) dropped after 2 hours to 34° C. and remained low until the animals died.

In group D (feces simultaneously with mesna) the temperature dropped to 34.5° C. on the first day, and dropped further in the surviving animals to 34° C. on the second and the third day until the rats died.

Group E animals (pretreated with mesna for three days and then given the lethal dose of faces) showed a decrease in body temperature to 34.5° C. on the first day, but recovered on the second day to 37.5° C., the normal temperature of the healthy untreated or only mesna treated rats.

The foregoing example demonstrates the efficacy of mesna in preventing peritonitis.

Adverting to FIG. 1, in the control wherein the peritoneum is contaminated with feces and mesna is not administered, one will observe the survival rate from 24 hours on is 0 percent. It was observed that the administration of mesna, alone, results in 100 percent survival after a period of 144 hours. On the other hand, notwithstanding the administration of mesna before the rats' contamination with feces, the survival rate is lowered to 90 percent from 24 to 36 hours and approximately 80 percent thereafter. When mesna is administered concomitantly with feces contamination, the survival rate drops to about 50 percent from 34 to 36 hours, followed by about 20 percent from 36 to 60 hours and 10 percent thereafter.

With reference to FIG. 2a, the GFR data on rats were derived by clamping the left renal artery for 45 minutes to induce ischemia in the kidney. The right kidney was untreated and served as the control. After 45 minutes, the clamp is removed and reperfusion commences for 90 minutes. During the experiment, urine and blood samples are collected so that GFR and fractional excretion of sodium (FENa) can be calculated at various intervals of time. From the control ischemic group, it is found that ischemia caused a decrease in GFR, from 0.79±0.08 to 0.19±0.04 ml/min, calculated after 90 min. of reperfusion. That is, only 24% recovery is demonstrated, based upon the control kidney.

However, when the rat is treated 30 minutes before occlusion with 180 mg/kg mesna, the GFR of the right control kidney is improved to 1.04±0.08 ml/min and the ischemic kidney is improved to 0.6±0.13, which is 60% of the control kidney. This is considered to be a very good improvement compared to those achieved with any other reagents used in the literature. Comparable results are shown when 60 mg/kg mesna is administered 30 minutes before occlusion.

Figure 2B:
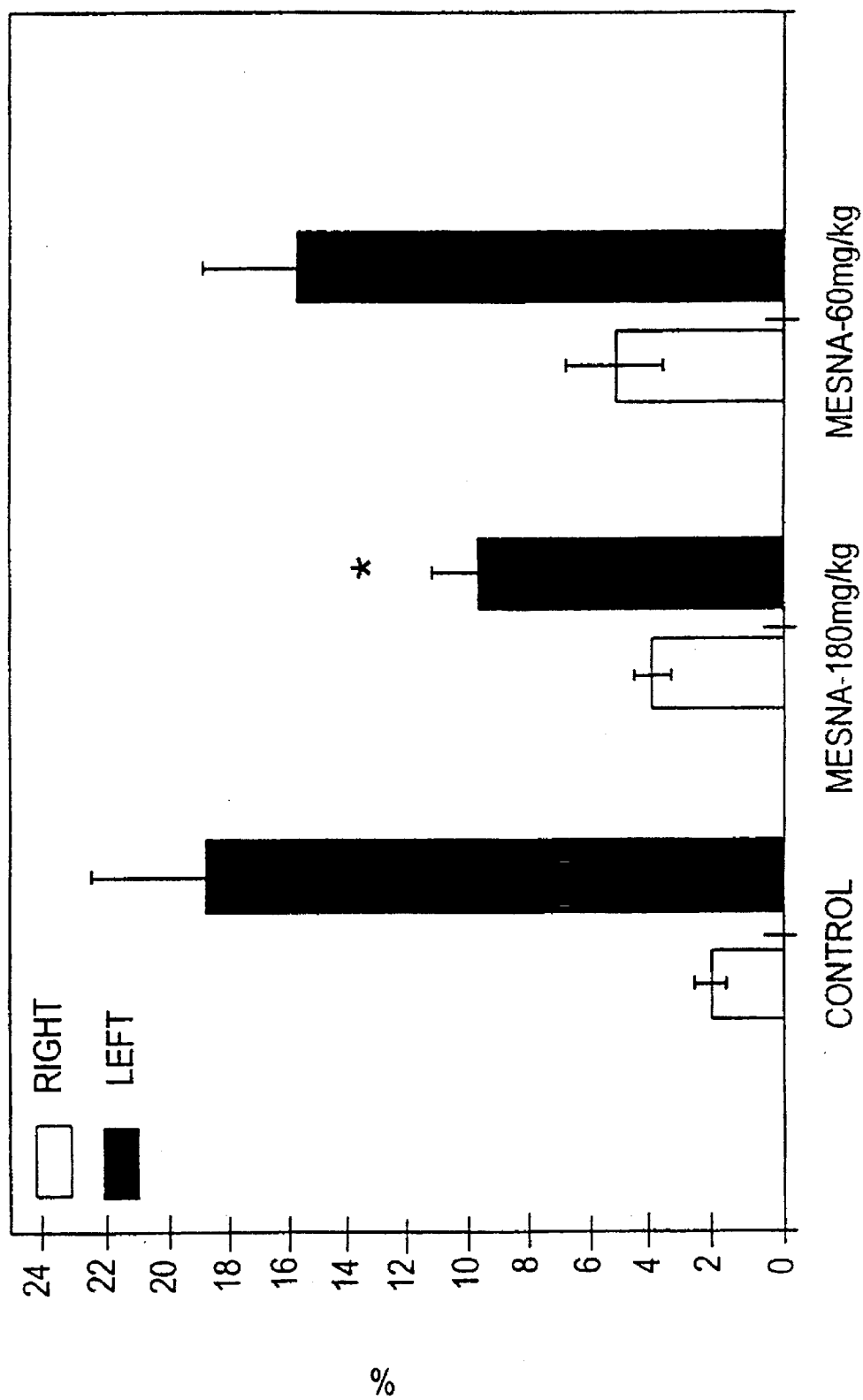

With respect to FIG. 2b, the ischemic kidney in the control group excreted sodium 9.5 fold more than the right non-occluded kidney. On the other hand, when mesna was administered 30 minutes before occlusion, at 180 mg/kg, the ischemic kidney excreted only 2.5 fold more sodium than the control unclamped right kidney, almost 4 fold improvement in fractional excretion of sodium (the fractional excretion of the right kidney when mesna was injected was higher than control non-treated with mesna, due to sodium load as mesna is a sodium salt; in this case it doesn't indicate tubular damage). At the dose of 60 mg/kg mesna, the ischemic kidney excreted 3.4 fold more sodium than the control kidney which constitutes a 2.8 fold improvement in the tubular function.

Thus, according to the present invention, mesna is employed in therapeutically effective amounts to avoid reperfusion injury in a donor organ following transplantation, particularly of a kidney. Advantageously, mesna can also be employed to avoid reperfusion injury in a donor organ subjected to ischemia subsequent to removal from a donor and prior to implantation in a recipient, by incorporating a therapeutically effective amount of mesna in the preservation solution in which the organ is maintained. Mesna can also be employed to avoid reperfusion injury to an organ subject to ischemia due to a medical procedure. In addition, mesna can be employed to avoid peritonitis in a patient, including prior or subsequent to violation of the peritoneum.

Only the preferred embodiments of the invention and but a few examples of versatility are shown and described in the present disclosure. It is to be understood that the invention is capable of use in various other combinations and environments and is capable of changes or modifications within the scope of the inventive concept as expressed herein.

We claim:

1. A method for avoiding reperfusion injury in a donor organ following transplantation of said organ, which method comprises periodically administering a therapeutically effective amount of the compound mesna to the patient-recipient of the transplanted organ.

2. The method according to claim 1, wherein the transplanted organ is a kidney.

3. The method according to claim 1, comprising initially administering mesna at a dosage of about 60 to about 180 mg/kg.

4. The method according to claim 3, comprising initially administering mesna in a solution.

5. The method according to claim 3, further comprising administering mesna at a maintenance level dosage of about 30 mg/kg of body weight/hour subsequent to the initial administration.

6. The method according to claim 1, comprising administering mesna in a solution.

7. The method according to claim 1, comprising orally administering mesna in the form of a bolus.

8. The method according to claim 1, wherein the patient is a human.

9. A method for avoiding reperfusion injury in a donor organ subject to ischemia during the period prior to transplantation, which method comprises, maintaining the donor organ in a preservation solution after removal from the donor and prior to implantation in the recipient, wherein the preservation solution comprises a therapeutically effective amount of the compound mesna to prevent reperfusion injury.

10. The method according to claim 9, wherein the donor organ is a kidney.

11. The method according to claim 10, wherein the preservation solution comprises a therapeutically effective amount of mesna to prevent acute tubular necrosis of the donor kidney.

12. The method according to claim 9, wherein the organ is a human organ.

13. A method for avoiding reperfusion injury to an organ subject to ischemia due to a medical procedure that causes a decreased perfusion, which method comprises periodically administering, prior to, and optionally during and/or subsequent to, said medical procedure, a therapeutically effective amount of mesna to a patient about to undergo a medical procedure.

14. The method according to claim 13, wherein the organ is a kidney.

15. The method according to claim 14, wherein the medical procedure is dialysis.

16. The method according to claim 13, wherein the organ is a heart.

17. The method according to claim 16, wherein the medical procedure is open-heart surgery.

18. The method according to claim 13, wherein the patient is a human.

19. A method for avoiding peritonitis in a patient, which method comprises periodically administering to said patient a therapeutically effective amount of the compound mesna prior to violation of the patient's peritoneum.

20. The method according to claim 19, comprising administering mesna at a dosage of about 120 mg/kg three times daily.

21. The method according to claim 19, wherein the patient is a human.

22. A method for avoiding peritonitis in a patient whose peritoneum has been violated, which method comprises periodically administering to said patient a therapeutically effective amount of the compound mesna.

23. The method according to claim 22, wherein the dosage of mesna administered is 120 mg/kg three times daily.

24. The method according to claim 22, wherein the patient is a human.

25. A method of transplanting an organ, which method comprises:

removing the organ from a donor; maintaining the organ in a preservation solution; and implanting the organ in a recipient, wherein the preservation solution comprises a therapeutically effective amount of the compound mesna to prevent reperfusion injury in the organ due to ischemia.

26. A method for avoiding acute renal failure due to ischemia, which method comprises periodically administering a therapeutically effective amount of mesna to a patient.

27. A method of transplanting an organ from a donor to a recipient, comprising periodically administering to the recipient a therapeutically effective amount of the compound mesna to avoid reperfusion injury to the organ, prior to and/or subsequent to transplantation.

28. The method according to claim 27, wherein mesna is administered prior to transplantation.

29. The method according to claim 27, wherein mesna is administered subsequent to transplantation.

30. A method of conducting a medical procedure that causes a decreased perfusion to an organ comprising administering to the patient, prior to, during and subsequent to undergoing the medical procedure, a therapeutically effective amount of mesna to avoid reperfusion injury to the organ.

31. A method according to claim 30, wherein the organ is a kidney and the medical procedure exposes the patient to a high risk of developing ischemic renal failure.

* * * * *